(12) United States Patent
Kida et al.

(10) Patent No.: US 11,511,195 B2
(45) Date of Patent: Nov. 29, 2022

(54) GAME DEVICE, METHOD, AND NON-TRANSITORY COMPUTER READABLE MEDIUM

(71) Applicant: JVCKENWOOD Corporation, Yokohama (JP)

(72) Inventors: Shingo Kida, Yokohama (JP); Hideki Aiba, Yokohama (JP); Ryouji Hoshi, Yokohama (JP); Hisashi Oka, Yokohama (JP); Yuya Takehara, Yokohama (JP); Yincheng Yang, Yokohama (JP); Hideya Tsujii, Yokohama (JP); Daisuke Hachiri, Yokohama (JP); Ryotaro Futamura, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 0 days.

(21) Appl. No.: 17/211,532

(22) Filed: Mar. 24, 2021

(65) Prior Publication Data

US 2021/0299570 A1 Sep. 30, 2021

(30) Foreign Application Priority Data

Mar. 26, 2020 (JP) .............................. JP2020-055349

(51) Int. Cl.
*A63F 13/67* (2014.01)
*A63F 13/54* (2014.01)
*A63F 13/533* (2014.01)
*A61B 5/16* (2006.01)
*A63F 13/837* (2014.01)

(52) U.S. Cl.
CPC .............. *A63F 13/67* (2014.09); *A61B 5/162* (2013.01); *A61B 5/165* (2013.01); *A63F 13/533* (2014.09); *A63F 13/54* (2014.09); *A61B 2503/12* (2013.01); *A63F 13/837* (2014.09); *A63F 2300/308* (2013.01); *A63F 2300/6027* (2013.01); *A63F 2300/6081* (2013.01); *A63F 2300/8076* (2013.01)

(58) Field of Classification Search
CPC .. A63F 13/67; A63F 13/79; A63F 2300/6027; A61B 5/165
See application file for complete search history.

(56) References Cited

U.S. PATENT DOCUMENTS

| 10,470,679 | B2 * | 11/2019 | Alberts | ................ A61B 5/1124 |
| 10,872,499 | B1 * | 12/2020 | Russ | ....................... G06F 3/011 |
| 2006/0281543 | A1 * | 12/2006 | Sutton | ................ G07F 17/3239 |
| | | | | 463/29 |
| 2014/0330159 | A1 * | 11/2014 | Costa | ...................... A61B 5/16 |
| | | | | 600/595 |

FOREIGN PATENT DOCUMENTS

JP 2011104170 A 6/2011

* cited by examiner

*Primary Examiner* — James S. McClellan
(74) *Attorney, Agent, or Firm* — Procopiop, Cory, Hargreaves & Savitch LLP

(57) ABSTRACT

The game device includes a reception unit that is configured to receive instruction information created when a user performs an operation on an input device triggered by a sound output while a game progresses and a derivation unit that is configured to start measuring the degree of fatigue on the basis of the instruction information received by the reception unit and derive the degree of fatigue of the user on the basis of an operation performed by the user during the started measurement of the degree of fatigue.

17 Claims, 9 Drawing Sheets

GAME DEVICE, METHOD, AND NON-TRANSITORY COMPUTER READABLE MEDIUM

CROSS-REFERENCE TO RELATED PATENT APPLICATIONS

This application claims priority from Japanese Application No. 2020-055349, filed on Mar. 26, 2020, the contents of which are incorporated by reference herein in its entirety.

BACKGROUND OF THE INVENTION

Field of the Invention

The present invention relates to a game device, a method, and a program.

Description of Related Art

A technique for games to prevent players from being excessively enthusiastic about playing games is known (e.g., refer to Patent Document 1). In this technique, a display unit displays figures having a predetermined size at short time intervals. If an operation instruction of a player received by a reception unit before a next figure is displayed matches an operation instruction corresponding to the direction indicated by the figure being displayed, an updating unit determines that the operation instruction is successful, and updates a success rate indicating statistical information stored in a storage unit. If a change of the success rate acquired by an acquisition unit significantly increases, a warning unit estimates that the player is too close to the screen, and if a change of a success rate significantly decreases, the warning unit estimates that the player is fatigued. The warning unit gives a warning with the estimation result. A plurality of figures are displayed on the screen only for a predetermined time period. That is, a "success" is determined when an operation that matches a displayed figure is made, and a warning is issued to the user on the basis of a change of a success rate.

PATENT DOCUMENTS

[Patent Document 1] Japanese Unexamined Patent Application, First Publication No. 2011-104170

SUMMARY OF THE INVENTION

A success rate is indicated by an index in which both "whether a user is aware of display of a figure" and "correctness of a reaction" are mixed. Thus, there is concern that it is not possible to correctly measure fatigue when a user fails to be aware of display of a figure, or the like. As a result that it is not possible to correctly measure fatigue, there is concern that the user will continue playing the game with fatigue and shortage of concentration.

An aspect of the embodiment of present invention is a game device including a reception unit that is configured to receive instruction information created when a user performs an operation on an input device triggered by a sound output while a game progresses, and a derivation unit that is configured to start measuring the degree of fatigue on the basis of the instruction information received by the reception unit and derive the degree of fatigue of the user on the basis of an operation performed by the user during the started measurement of the degree of fatigue.

An aspect of embodiment of the present invention is a method including receiving instruction information created when a user performs an operation on an input device triggered by a sound output while a game progresses, and starting measuring the degree of fatigue on the basis of the instruction information and deriving the degree of fatigue of the user on the basis of an operation performed by the user during the started measurement of the degree of fatigue.

An aspect of the present invention is a non-transitory computer readable medium, storing a program causing a computer to execute receiving instruction information created when a user performs an operation on an input device triggered by a sound output while a game progresses and starting measuring a degree of fatigue on the basis of the instruction information and deriving a degree of fatigue of the user on the basis of an operation performed by the user during the started measurement of a degree of fatigue.

According to the embodiment of present invention, it is possible to provide a game device, a method, and a program that enable the degree of fatigue to be measured while a game progresses.

DETAILED DESCRIPTION OF THE INVENTION

Figure 1:
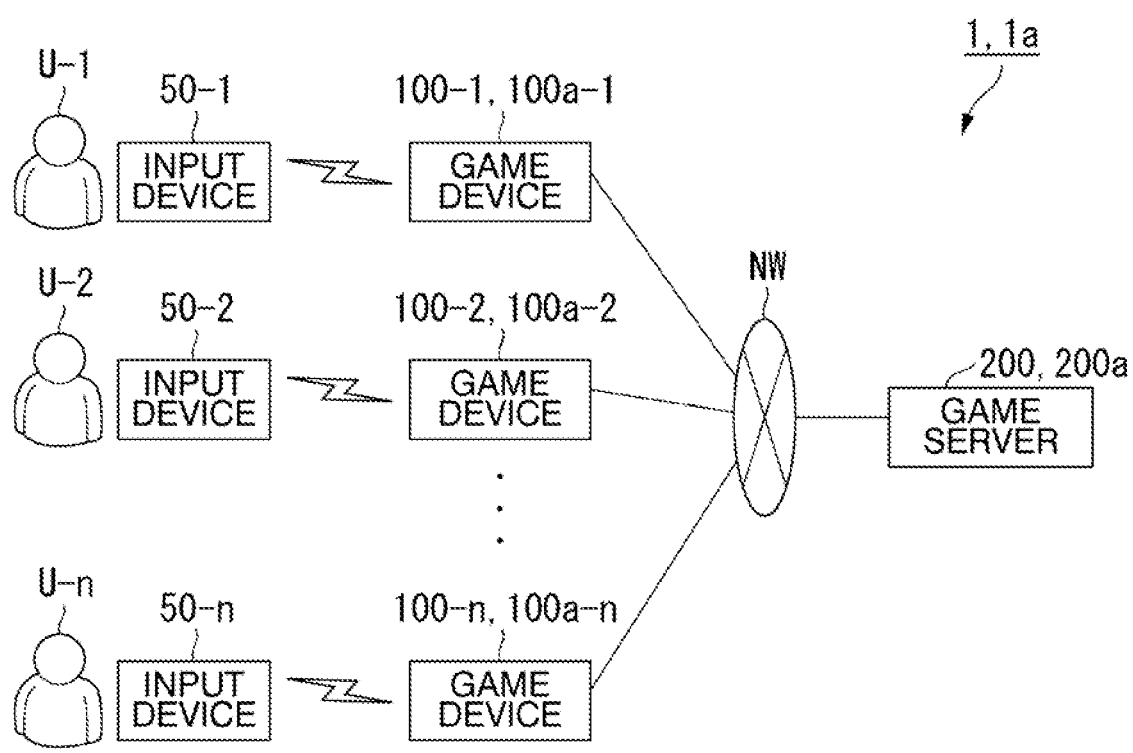
FIG. 1 is a diagram illustrating a configuration example of a game system according to an embodiment of the present invention.

Next, a game device, a method, and a program according to embodiments will be described with reference to drawings. The embodiments described below are merely examples, and an embodiment to which the present invention is applied is not limited to the following embodiments.

Further, the same reference numerals are used for constituent elements having the same functions in all of the drawings showing the embodiments, and a repetitive description thereof will be omitted.

In addition, "on the basis of XX" in the present specification means "on the basis of at least XX" and includes a case on the basis of another element in addition to "XX." In addition, "on the basis of XX" is not limited to a case in which XX is directly used, and also includes a case on the basis of an arithmetic operation or in which processing is performed on XX. "XX" is any element (e.g., any information).

Embodiment

Game System

FIG. 1 is a diagram illustrating a configuration example of a game system according to an embodiment of the present invention. In FIG. 1, a game system 1 includes an input device 50-1, an input device 50-2, ..., and an input device 50-n, (n is an integer satisfying n>0), a game device 100-1, a game device 100-2, ..., and a game device 100-n, and a game server 200.

The input device 50-1, the input device 50-2, ..., and the input device 50-n are connected to the game device 100-1, the game device 100-2, ..., and the game device 100-n, respectively. As an example, a case in which the input device 50-1, the input device 50-2, ..., and the input device 50-n are wirelessly connected to the game device 100-1, the game device 100-2, ..., and the game device 100-n, respectively, will be described below. However, the input device 50-1, the input device 50-2, ..., and the input device 50-n may be connected to the game device 100-1, the game device 100-2, ..., and the game device 100-n, respectively, by wires.

In addition, the game device 100-1, the game device 100-2, ..., and the game device 100-n communicate with the game server 200 via a network NW. However, the game device 100-1, the game device 100-2, ..., and the game device 100-n may be connected to the game server 200 without passing through the network NW. As an example, description of a case in which the game device 100-1, the game device 100-2, ..., and the game device 100-n communicate with the game server 200 via the network NW by wires will be continued. However, the game device 100-1, the game device 100-2, ..., and the game device 100-n may wirelessly communicate with the game server 200 via the network NW.

The network NW includes, for example, the Internet, a wide area network (WAN), a local area network (LAN), provider equipment, a radio base station, and the like.

The input device 50-1 is connected to the game device 100-1 by wires or wirelessly. A user U-1 uses the game device 100-1 and the input device 50-1. The input device 50-2 is connected to the game device 100-2 by wires or wirelessly. A user U-2 uses the game device 100-2 and the input device 50-2. The input device 50-n is connected to the game device 100-n by wires or wirelessly. A user U-n uses the game device 100-n and the input device 50-n.

Hereinafter, any game device among the game device 100-1 to the game device 100-n will be described as a game device 100. In addition, an input device connected to the game device 100 will be described as an input device 50, and a user using the game device 100 and the input device 50 will be described as a user U. In addition, description of a case in which the input device 50 is wirelessly connected to the game device 100 will be continued.

The user U performs an operation on the input device 50 triggered by a sound output while a game progresses. Here, an example of the game is a simulation game (shooting game). A simulation game (shooting game) is one of genres of computer games in which a user shoots down enemy planes with bullets, laser, or the like. It may be a first-person shooter (FPS) or a third-person shooter (TPS). Here, the first-person shooter refers to an action game in which a user playing as the main character can arbitrarily move in the world and space in the game and fight using weapons, bare hands, or the like in his or her perspective (first person). In the first-person shooter, basically only a part of the player character such as the arms and a weapon or a tool are displayed on the screen. Here, the third-person shooter refers to an action game in which a user can arbitrarily move in the world and space in the game and fight using weapons, bare hands, or the like in a third-person perspective tracing the main character in the game or the like.

The input device 50 detects an operation performed by the user U and creates instruction information including the user ID and information indicating content of the operation on the basis of the detected operation. The input device 50 outputs the created instruction information to the game device 100. The game device 100 transmits the instruction information to the game server 200 upon receiving the instruction information output by the input device 50. The game server 200 receives the instruction information transmitted by the game device 100 and reflects the content of the operation in the game on the basis of the information indicating the content of the operation included in the received instruction information. The game server 200 transmits game information including game data in which the content of the operation is reflected to the game device 100 that has transmitted the instruction information. The game device 100 receives the game information transmitted by the game server 200 and outputs an image and sound of the game on the basis of the game data included in the received game information.

In addition, the game device 100 starts measuring the degree of fatigue. Here, the degree of fatigue is an index indicating the degree of fatigue of the user U. As the degree at which the user U immerses himself or herself in the game becomes higher, the degree of fatigue becomes lower. On the other hand, even if the user U is immersing himself or herself in the game, if the speed or accuracy of an operation of the user U becomes lower due to (physical or mental) fatigue, the degree of fatigue becomes higher. Further, the degree of fatigue may be the degree of concentration that is an index indicating the degree of the user U focusing on and working on a game. As the degree at which the user U immerses himself or herself in the game becomes higher, the degree of concentration becomes higher. On the other hand, even if the user U is immersing himself or herself in the game, if the speed or accuracy of an operation of the user U becomes lower due to (physical or mental) fatigue, the degree of fatigue becomes lower.

The user U continues the game by performing an operation on the input device 50. The input device 50 detects the operation performed by the user U and creates instruction information on the basis of the detected operation. The input device 50 outputs the created instruction information to the game device 100.

The game device 100 receives the instruction information output by the input device 50. The game device 100 derives the degree of fatigue on the basis of the information indicating the content of the operation included in the received instruction information. The game device 100 outputs information indicating the derived degree of fatigue.

Each of the input device 50, the game device 100, and the game server 200 included in the game system 1 will be sequentially described below.

Input Device 50

An example of the input device 50 includes a left grip part and a right grip part. The user U grips the left grip part with the left hand and the right grip part with the right hand to operate the input device 50. Direction keys and operation buttons are provided on the top surface of the housing of the input device 50. Furthermore, a touch pad is provided in a flat area between the direction keys and the operation buttons provided on the top surface of the housing of the input device 50. The input device 50 detects an operation performed by the user U and creates instruction information including the user ID and information indicating the content of the operation on the basis of the detected operation. The input device 50 transmits the created instruction information wirelessly to the game device 100.

Game Device 100

Figure 2:
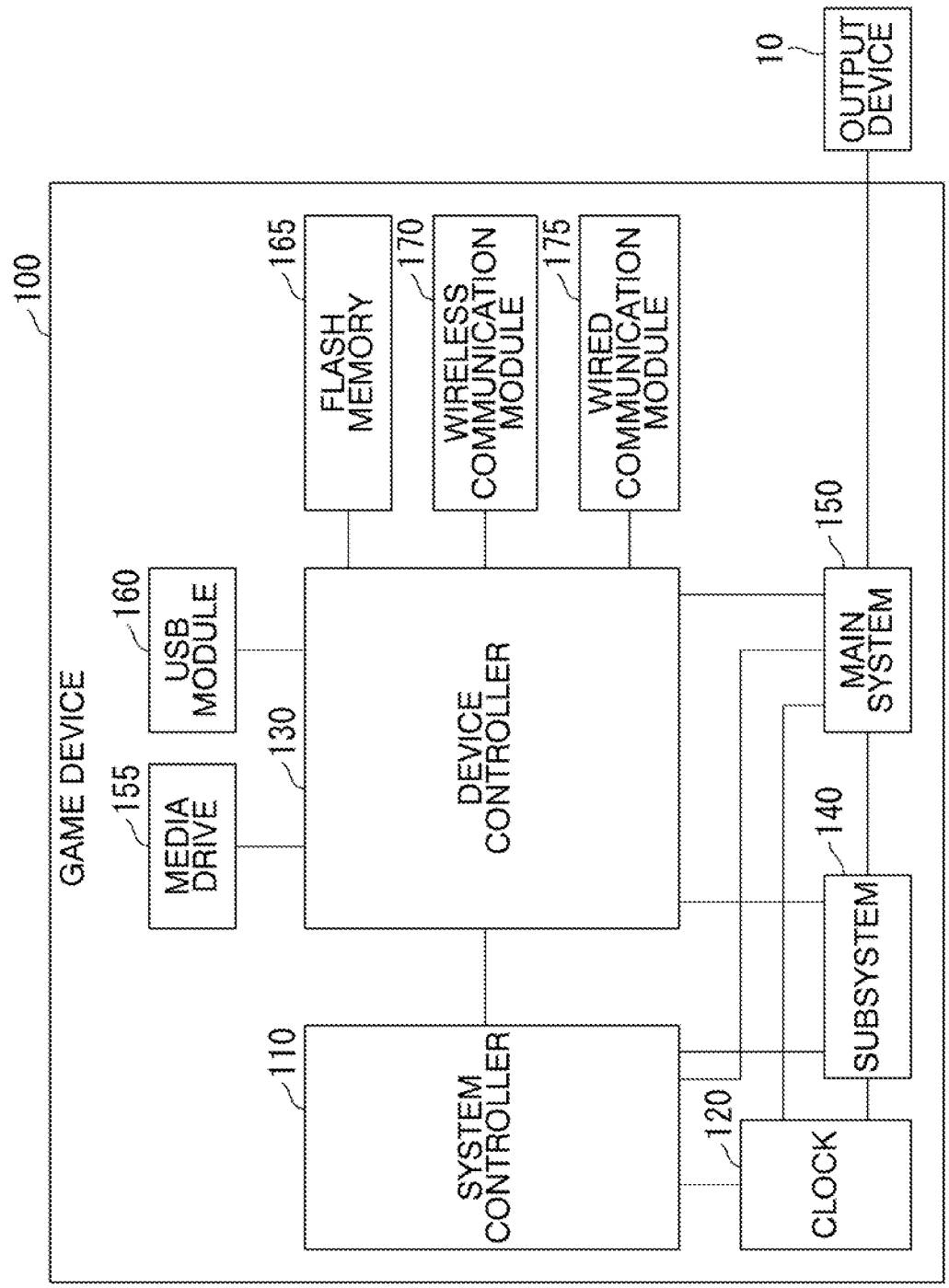
FIG. 2 is a diagram illustrating an example of a game device according to the present embodiment.

FIG. 2 is a diagram illustrating an example of the game device according to the present embodiment. In FIG. 2, a hardware configuration of the game device 100 is mainly illustrated.

The game device 100 includes a system controller 110, a clock 120, a device controller 130, a media drive 155, a USB module 160, a flash memory 165, a wireless communication module 170, a wired communication module 175, a subsystem 140, and a main system 150.

The main system 150 includes a main central processing unit (CPU), a memory, a main controller, a graphics processing unit (GPU), and the like. The CPU mainly executes arithmetic operation processing of a game program. These functions are configured in a system-on-chip to be formed on one chip. The main CPU executes game programs. The main system 150 outputs a result of arithmetic operation processing of a game program and an execution result of the game program to an output device 10. An example of the output device 10 is a monitor with a display that outputs images and a speaker that outputs sound.

The subsystem 140 includes a sub CPU, a memory, a memory controller, and the like. The subsystem 140 neither includes a GPU nor executes a game program. The sub CPU operates even while the main CPU is in a standby state, and limits processing functions of operations to reduce power consumption to a low level.

The system controller 110 detects a power-on instruction or a power-off instruction when the user U presses a main power button (not illustrated). The system controller 110 turns on or off power of the game device 100 on the basis of the detected power-on instruction or power-off instruction.

An example of the clock 120 is a real-time clock. The clock 120 generates current day and time information and outputs the generated current day and time information to the system controller 110, the subsystem 140, and the main system 150.

An example of the device controller 130 is configured by a large-scale integrated circuit (LSI) and executes transfer of information between devices. The device controller 130 is connected to devices such as the system controller 110, the media drive 155, the USB module 160, the flash memory 165, the wireless communication module 170, the wired communication module 175, the subsystem 140, the main system 150, and the like. The device controller 130 absorbs a difference in electrical characteristics and a difference in data transfer speed between the devices, and controls timings of data transfer.

The media drive 155 is loaded with a ROM medium in which application software such as a game and license information are recorded. The media drive 155 reads the program, data, and the like from the loaded ROM medium. The ROM medium is a recording medium dedicated to reading such as an optical disc, a magneto-optical disc, or the like.

The USB module 160 is a module connecting to an external apparatus with a USB cable. The USB module 160 may be connected to a device such as an auxiliary storage device (not illustrated) or a camera (not illustrated) with a USB cable.

The flash memory 165 is an auxiliary storage device that configures an internal storage.

The wireless communication module 170 communicates with an external apparatus such as the input device 50 wirelessly in a wireless communication method such as a wireless LAN, Bluetooth (registered trademark), or LTE (registered trademark).

The wired communication module 175 is connected to an external apparatus and communicates with the connected input device 50 by wires.

Figure 3:
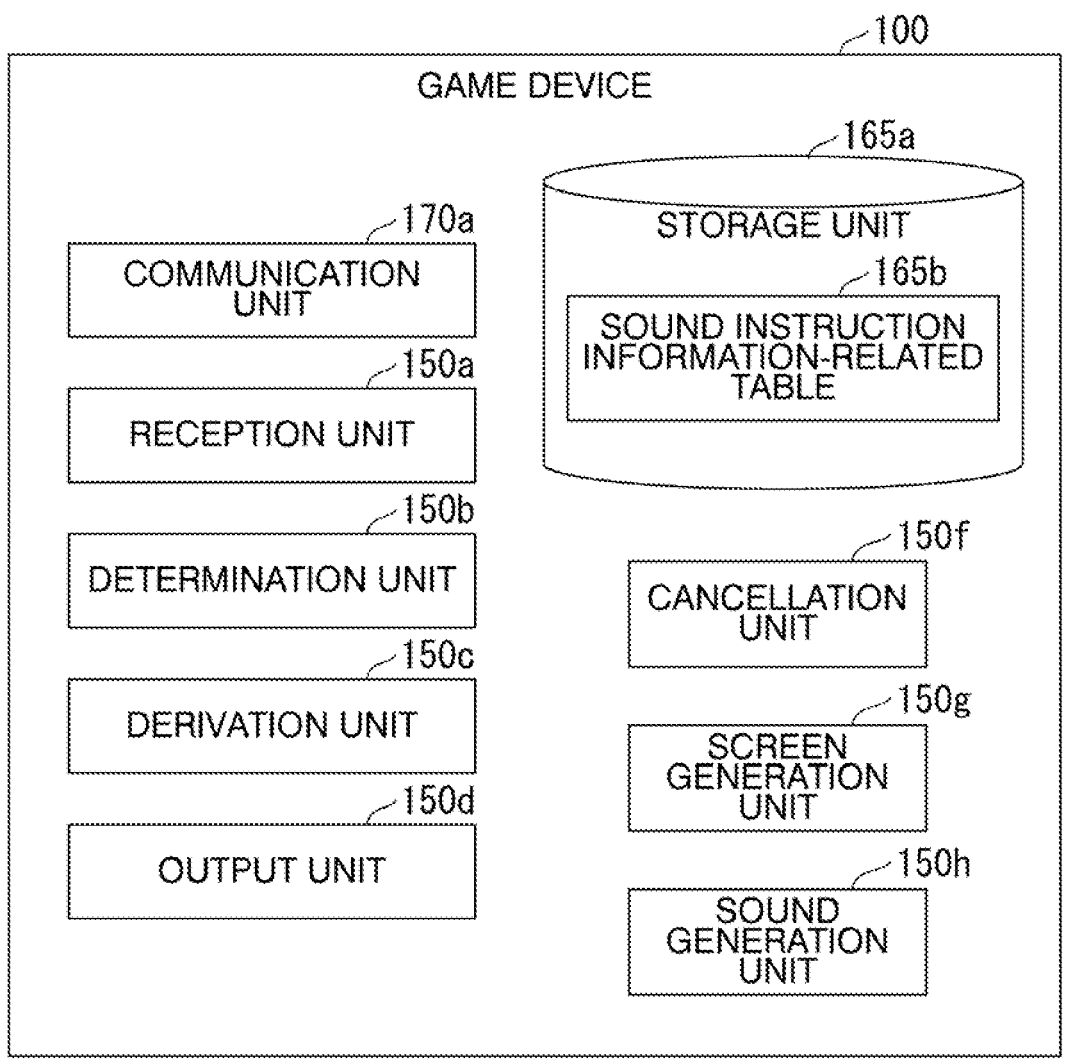
FIG. 3 is a block diagram illustrating an example of the game device according to the present embodiment.

FIG. 3 is a block diagram illustrating an example of the game device according to the present embodiment. In FIG. 3, a functional configuration of the game device 100 is mainly illustrated.

The game device 100 includes, for example, a communication unit 170*a*, a reception unit 150*a*, a determination unit 150*b*, a derivation unit 150*c*, an output unit 150*d*, a cancellation unit 150*f*, a screen generation unit 150*g*, a sound generation unit 150*h*, and a storage unit 165*a*.

The communication unit 170*a* is realized by, for example, the wireless communication module 170 and the wired communication module 175. The communication unit 170*a* communicates with an external communication device such as the input device 50. In addition, the communication unit 170*a* communicates with an external communication device such as the game server 200 via the network NW. The communication unit 170*a* communicates in a wireless communication method, for example, a wireless LAN, Bluetooth (registered trademark), LTE (registered trademark), or the like. The communication unit 170*a* receives instruction information transmitted by the input device 50. The communication unit 170*a* transmits the instruction information to the game server 200. The communication unit 170*a* receives game information transmitted by the game server 200.

An example of the storage unit 165*a* is realized by the flash memory 165. The storage unit 165*a* may be realized by a hard disk drive (HDD), a random access memory (RAM), a read only memory (ROM), or the like. The storage unit 165*a* saves data to be used by game programs, a sound instruction information-related table 165*b*, and the like. The data to be used by game programs, the sound instruction information-related table 165*b*, and the like may be stored on a cloud.

The sound instruction information-related table 165*b* is information in a table form in which one or a plurality of sound IDs are associated with information indicating content of an operation required for the user U when a sound corresponding to each of the one or the plurality of sound IDs is output. A sound ID is sound identification information. The information indicating the content of an operation is information indicating the operation required for the user when a sound corresponding to a sound ID is output from the game device 100. The sound includes a speech.

The reception unit 150*a*, the determination unit 150*b*, the derivation unit 150*c*, the output unit 150*d*, the cancellation unit 150*f*, the screen generation unit 150*g*, and the sound generation unit 150*h* are realized by, for example, the main system 150 executing a computer program (software) saved in the storage unit 165a. In addition, some or all of these functional units may be realized by hardware (circuit unit including circuitry) such as an LSI, an ASIC, an FPGA, or a GPU, or may be realized by collaboration of software and hardware. The computer program may be saved in a storage device such as an HDD or a flash memory in advance, may be saved in a detachable storage medium such as a DVD or a CD-ROM, or may be installed by loading a storage medium in a drive device.

The reception unit 150a receives instruction information received by the communication unit 170a. The reception unit 150a receives game information received by the communication unit 170a.

The determination unit 150b acquires information indicating the content of an operation stored in association with a sound ID corresponding to a sound output while the game progresses from the sound instruction information-related table 165b of the storage unit 165a. The determination unit 150b determines whether the acquired information indicating the content of the operation matches the information indicating the content of the operation included in the instruction information received by the reception unit 150a. If it is determined that the information matches, the determination unit 150b determines to start measuring the degree of fatigue.

In addition, the determination unit 150b may determines whether the information indicating the content of the operation included in the instruction information received by the reception unit 150a corresponds to an operation to cancel the measurement of the degree of fatigue.

If the determination unit 150b determines to start measuring the degree of fatigue of the user U, the derivation unit 150c starts measuring the degree of fatigue of the user U. After starting measuring the degree of fatigue, the derivation unit 150c determines whether an operation performed by the user U corresponds to a predetermined operation required for the user U in a scene of the game. The derivation unit 150c derives the degree of fatigue of the user U on the basis of the operation performed by the user U corresponding to the predetermined operation.

An example of the predetermined operation required for the user U in a scene of the game will be described.

Figure 4:
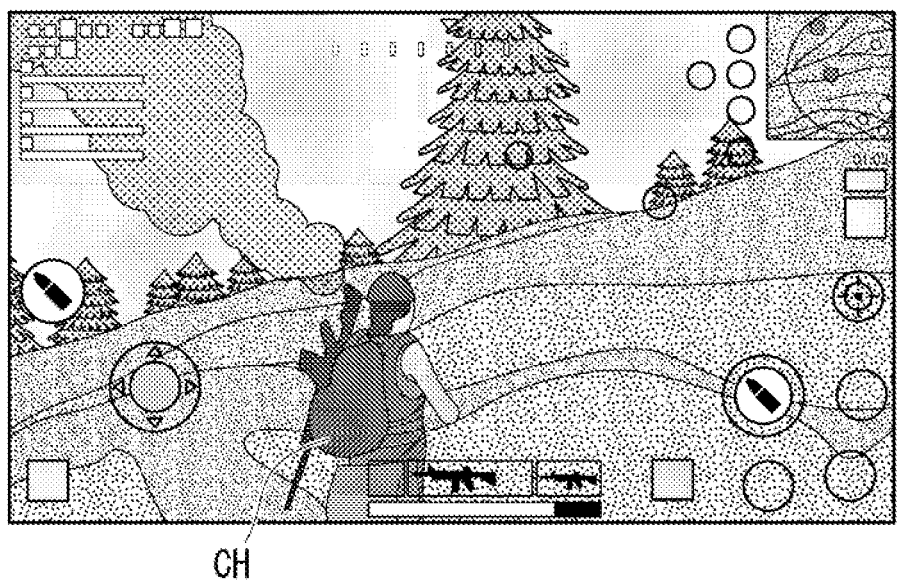
FIG. 4 illustrates an example of a scene of a game.

FIG. 4 illustrates an example of a scene of a game. An example of the game is a shooting game as described above. In FIG. 4, a third-person shooter is illustrated as an example of a shooting game. A third-person shooter basically adopts a viewpoint of looking down on a scene from behind and overhead an operation character CH, as illustrated in FIG. 4. A third-person shooter employs camerawork in which an operation character is displayed at the center of the screen in normal times. In a third-person shooter, a target is aimed at and shot.

A relationship between a sound that triggers measurement of the degree of fatigue and a predetermined operation required for the user U due to the sound will be described.

Figure 5:
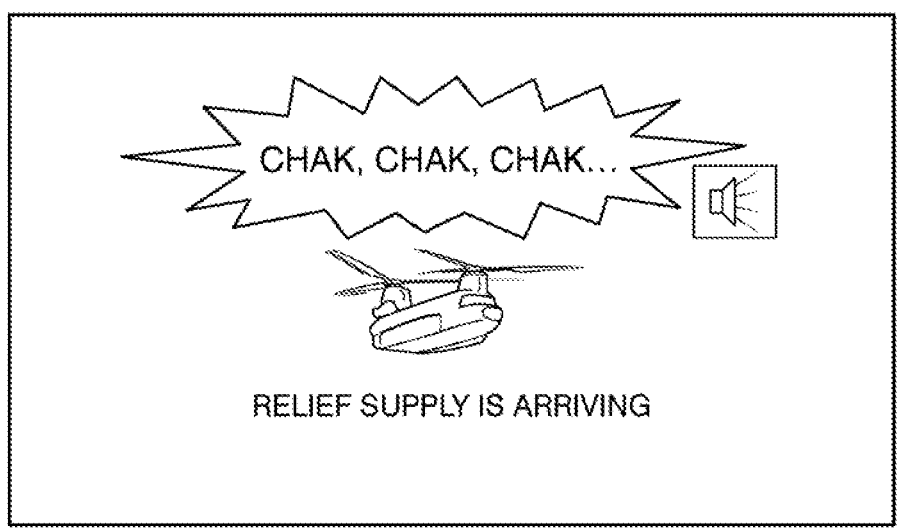
FIG. 5 is a diagram illustrating Example 1 of a predetermined operation required for a user.
Figure 5:
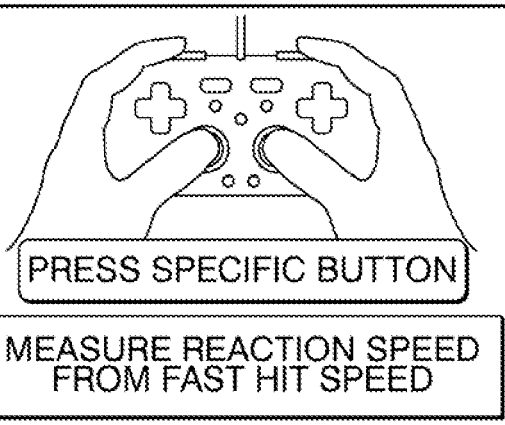

FIG. 5 is a diagram illustrating Example 1 of the predetermined operation required for the user. In the example illustrated in FIG. 5, the game device 100 requires the user U to continuously perform an operation of pressing a specific button by outputting sound of an aircraft such as a helicopter flying "chak, chak, chak, . . . " to the output device 10 in a scene of the game. In the aircraft, for example, relief supplies are piled up. That is, the game device 100 stores the sound ID corresponding to the sound "chak, chak, chak, . . . " in association with information indicating the content of the operation corresponding to the operation of continuously pressing the specific button.

The derivation unit 150c acquires sound output time information that is information indicating the time at which the sound was output to the output device 10 from the clock 120. In addition, after the sound is output to the output device 10, the derivation unit 150c acquires reception time information that is information indicating the time at which the reception unit 150a received the instruction information from the clock 120. The derivation unit 150c counts the number of times in which the information indicating the content of the operation included in the instruction information received by the reception unit 150a corresponds to the information indicating the content of the operation stored in association with the sound ID of the sound in the period from the time at which the sound output time information or the reception time information was acquired to a predetermined time (which will be referred to as a "measurement time"). The derivation unit 150c derives a reaction speed by dividing the count result by the measurement time.

In addition, the derivation unit 150c may derive the elapsed time from the time at which an event is started as the output device 10 outputs the sound to the time at which the event is cleared due to a predetermined number of repeated hit operations. The event is cleared on the basis of the information indicating the content of the operation included in the instruction information received by the reception unit 150a because the content of the operation is reflected in the game. In this case, the derivation unit 150c may activate a timer at the timing at which the sound is output to the output device 10, turn off the timer at the timing at which the event is cleared after the timer is activated, acquire the elapsed time, and set the acquired elapsed time as a reaction speed.

Figure 6:
FIG. 6 is a diagram illustrating Example 2 of a predetermined operation required for a user.
Figure 6:
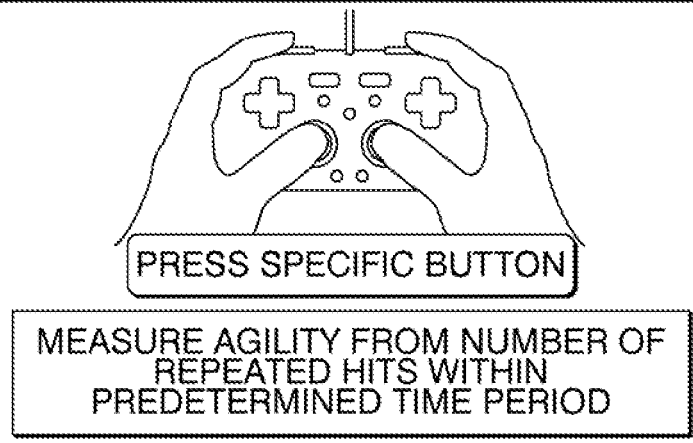

FIG. 6 is a diagram illustrating Example 2 of the predetermined operation required for the user. In the example illustrated in FIG. 6, the game device 100 requires the user U to perform an operation of repeatedly pressing a specific button by outputting a speech of a comrade calling for help "help" to the output device 10 in a scene of the game. That is, the game device 100 stores the sound ID corresponding to the speech "help" in association with information indicating content of an operation corresponding to the operation of repeatedly pressing the specific button.

The derivation unit 150c acquires sound output time information indicating the time at which the speech was output to the output device 10 from the clock 120. In addition, after the speech was output to the output device 10, the derivation unit 150c acquires reception time information indicating the time at which the reception unit 150a received the instruction information from the clock 120. The derivation unit 150c counts the number of time (the number of repeated hits) in which the information indicating the content of the operation included in the instruction information received by the reception unit 150a corresponds to the information indicating the content of the operation stored in association with the sound ID of the sound in a period from the time at which the sound output time information or the reception time information was acquired to a predetermined time (which will be referred to as a "measurement time" below). The derivation unit 150c derives an agility on the basis of the count result.

The derivation unit 150c derives the degree of fatigue of the user U on the basis of the reaction speed and the agility. The derivation unit 150c may, for example, derive the degree of fatigue of the user U on the basis of the reaction speed, may derive the degree of fatigue of the user U on the basis of the agility, or may derive the degree of fatigue of the user U on the basis of the reaction speed and the agility by performing a predetermined arithmetic operation. A ground for derivation is not limited to a reaction speed or an agility, and the degree of fatigue of the user U may be derived using the accuracy of an operation, such as shooting a predetermined target, drawing a predetermined trajectory, or operating an input unit in a predetermined order. Here, the case in which the degree of fatigue of the user U is derived on the basis of the reaction speed and the agility by performing a predetermined arithmetic operation will be described as an example. Returning to FIG. 3, description will be continued.

The output unit 150d acquires information indicating the degree of fatigue from the derivation unit 150c. The output unit 150d displays information indicating that the user U is encouraged to take a rest on the output device 10 in a case on the basis of the acquired degree of fatigue in which the degree of fatigue is equal to higher than a predetermined threshold value or a predetermined value obtained from a statistical value (representative value) such as a mean, median, maximum, or mode obtained from degrees of fatigue for a predetermined past period. In addition, the output unit 150d may display the information indicating that the user U is encouraged to take a rest on the output device 10 on the basis of the acquired degree of fatigue and the degrees of fatigue of the past in a case in which the degree of fatigue or the statistical value of the degrees of fatigue continuously increases for a predetermined time period or longer.

Figure 7:
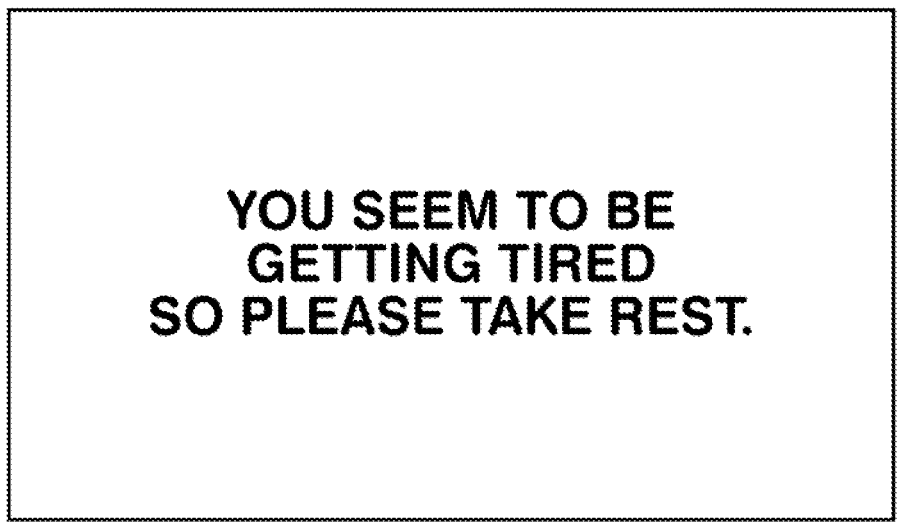
FIG. 7 is a diagram illustrating an example of information output by an output device.

FIG. 7 is a diagram illustrating an example of information output by the output device. In the example illustrated in FIG. 7, information indicating that the user U is encouraged to take a rest "You seem to be getting tired so please take a rest" is displayed on the output device 10. Instead of or along with the information indicating that the user U is encouraged to take a rest, information indicating that stopping the game is encouraged may be displayed on the output device 10. Returning to FIG. 3, a description will be continued.

The cancellation unit 150f cancels the measurement of the degree of fatigue if the determination unit 150b determines that the instruction information received by the reception unit 150a corresponds to an operation of canceling the measurement of the degree of fatigue. For example, the cancellation unit 150f may determine that there has not been an operation corresponding to the instruction information.

The screen generation unit 150g acquires the game information received by the reception unit 150a and generates images of the game controlled by the game server 200 on the basis of game data included in the acquired game information. The screen generation unit 150g outputs the generated images of the game to the output device 10.

The sound generation unit 150h acquires the game information received by the reception unit 150a and generates sound of the game controlled by the game server 200 on the basis of the game data included in the acquired game information. The sound generation unit 150h outputs the generated sound of the game to the output device 10.

Game Server 200

Figure 8:
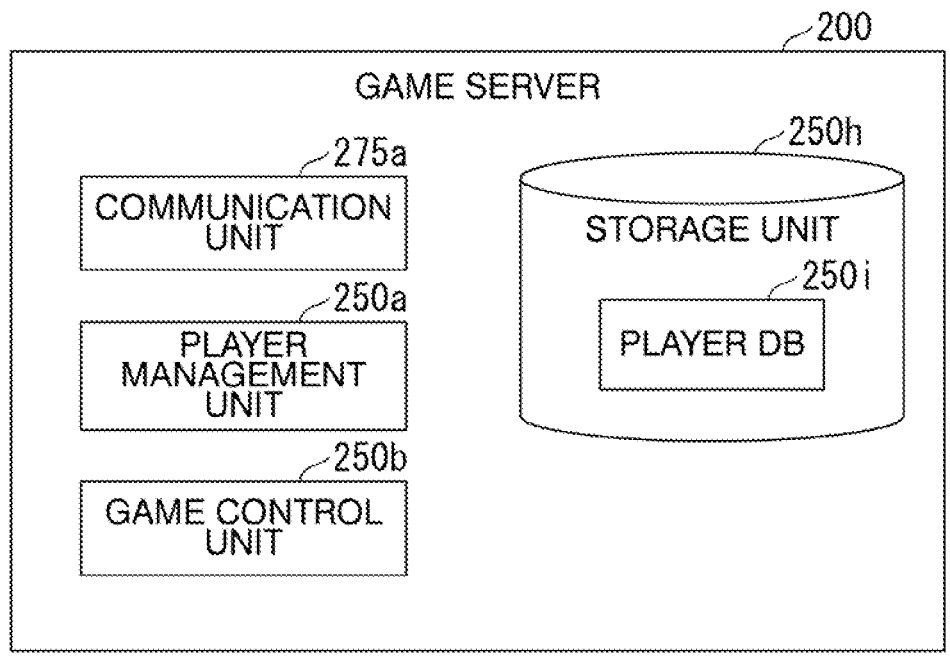
FIG. 8 is a diagram illustrating an example of a game server according to the present embodiment.

FIG. 8 is a diagram illustrating an example of the game server according to the present embodiment.

The game server 200 is realized by a device such as a personal computer, a server, a smartphone, a tablet computer, or an industrial computer. The game server 200 includes a communication unit 275a, a player management unit 250a, a game control unit 250b, and a storage unit 250h.

The communication unit 275a is realized by a communication module. The communication unit 275a communicates with an external communication device via the network NW. The communication unit 275a may communicate in a communication method, for example, a wired LAN, or the like. In addition, the communication unit 275a may communicate in a wireless communication method, for example, a wireless LAN, Bluetooth (registered trademark), LTE (registered trademark), or the like. Here, a case in which the communication unit 275a communicates in a communication method such as a wired LAN will be continuously described. The communication unit 275a holds communication information necessary to communicate with the game device 100 via the network NW. The communication unit 275a receives instruction information transmitted by the game device 100. The communication unit 275a acquires game information output by the game control unit 250b and transmits the acquired game information to the game device 100.

The storage unit 250h is realized by an HDD, a flash memory, a RAM, a ROM, or the like. The storage unit 250h stores a player DB 250i. The player DB 250i may be stored on a cloud.

The player DB 250i stores player IDs, passwords, game device addresses, and resources in association with each other. A player ID is identification information on a player of the game. A password is a sequence of letters, symbols, and numbers for authenticating a player. An example of a game device address is an IP address of the game device 100 to be used by a player. An ID of a device may be used as a game device address. A resource is the number of items owned by a player in the game, such as food, fuel, and wood.

The player management unit 250a and the game control unit 250b are realized by, for example, a hardware processor such as a CPU executing a computer program (software) saved in the storage unit 250h. In addition, some or all of these functional units may be realized by hardware (circuit unit including circuitry) such as an LSI, an ASIC, an FPGA, or a GPU, or may be realized by collaboration of software and hardware. The computer program may be saved in a storage device such as an HDD or a flash memory in advance, may be saved in a detachable storage medium such as a DVD or a CD-ROM, or may be installed by loading a storage medium in a drive device.

The player management unit 250a manages the user U of the game device 100. Upon receiving a log-in request included in instruction information transmitted by the game device 100, the player management unit 250a refers to the player DB 250i stored in the storage unit 250h to authenticate the user U of the game device 100. If the user U is successfully authenticated, the player management unit 250a allows log-in of the game device 100.

The game control unit 250b executes a game program for managing progress of the game. The game control unit 250b acquires the instruction information received by the communication unit 275a to cause the game to progress on the basis of the user ID included in the acquired instruction information and information indicating the content of the operation. The game control unit 250b creates game data indicating a game status of the game device 100. The game control unit 250b creates game information including the created game data and destined for the game device 100 corresponding to the game data. The game control unit 250b outputs the created game information to the communication unit 275a.

Operation of Game System 1

Figure 9:
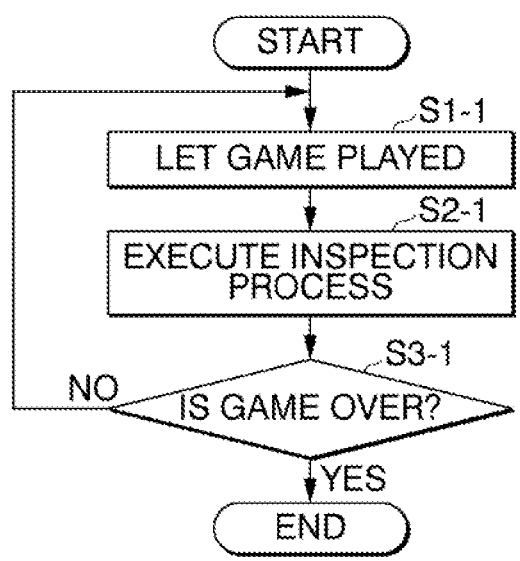
FIG. 9 is a flowchart showing Example 1 of an operation of the game system according to the present embodiment.

FIG. 9 is a flowchart showing Example 1 of an operation of the game system according to the present embodiment.

In FIG. 9, an example of an operation of the game device 100 is mainly shown. FIG. 9 shows an operation after log-in of the user U is completed.

Step S1-1

The game device 100 lets the game progress.

Step S2-1

The game device 100 executes an inspection process such as measurement of the degree of fatigue.

Step S3-1

The game device 100 determines whether the game is over. If the game is not over, the operation proceeds to step S1-1. If the game is over, the operation ends.

Figure 10:
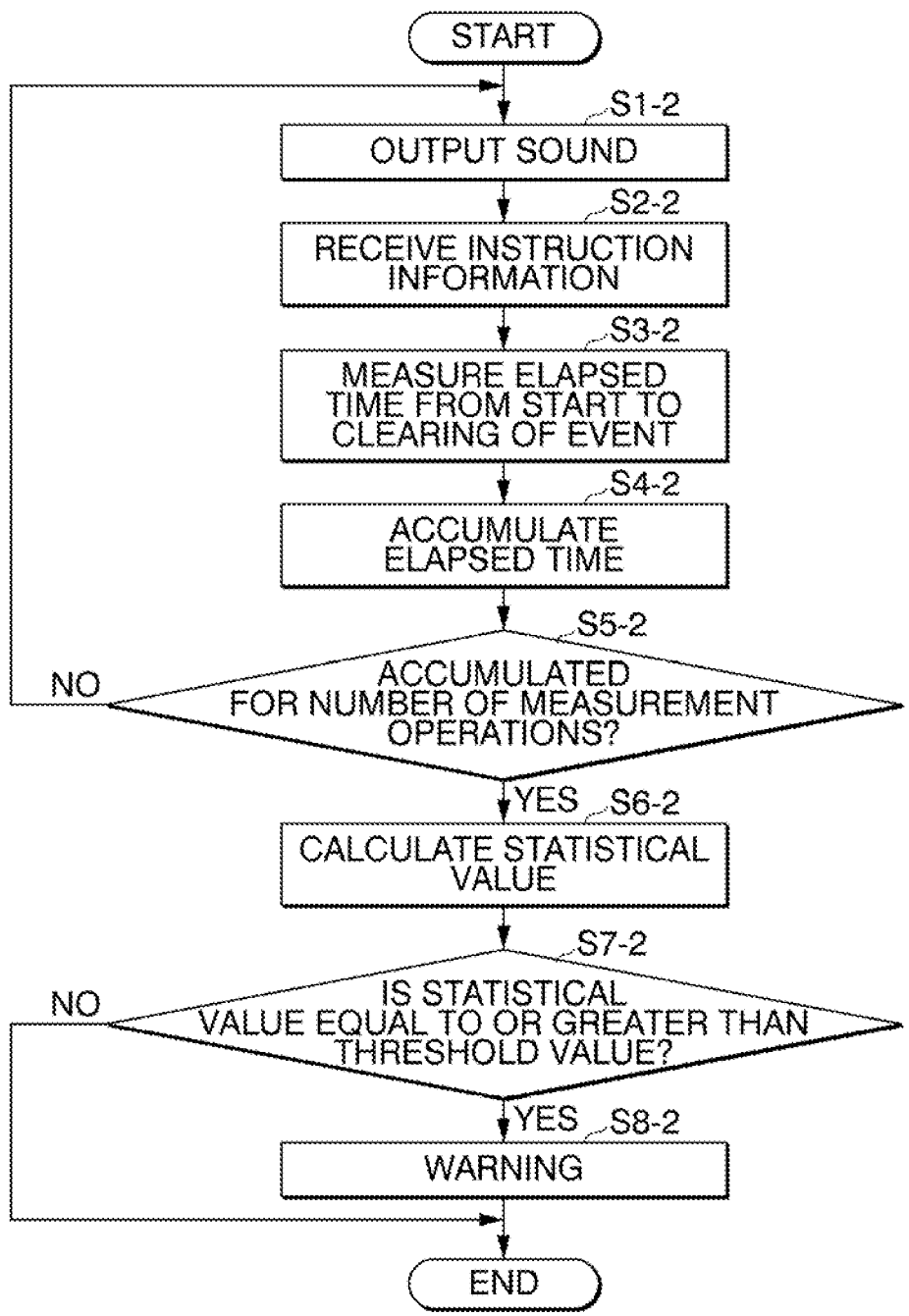
FIG. 10 is a flowchart showing Example 2 of an operation of the game system according to the present embodiment.

FIG. 10 is a flowchart showing Example 2 of an operation of the game system according to the present embodiment. In FIG. 10, details of the inspection process of step S2-1 of FIG. 9 are mainly described. Here, as an example, a case in which the derivation unit 150c starts an event by outputting a sound to the output device 10 and acquires an elapsed time from the time at which the event is started to the time at which the event is cleared will be described. The acquired elapsed time is regarded as a reaction speed.

Step S1-2

The game device 100 outputs a sound in a scene of the game.

Step S2-2

The reception unit 150a of the game device 100 receives instruction information received by the communication unit 170a. The determination unit 150b determines whether measurement of the degree of fatigue is to be started on the basis of information indicating content of an operation included in the instruction information received by the reception unit 150a. Here, a case in which the determination unit 150b determines that measurement of the degree of fatigue has been started will be continuously described.

Step S3-2

The derivation unit 150c of the game device 100 activates a timer at a timing at which a sound is output to the output device 10, turns off the timer at a timing at which the event is cleared due to a predetermined number of a repeated hit operations after the timer is activated, acquires the elapsed time, and sets the acquired elapsed time as a reaction speed.

Step S4-2

The derivation unit 150c of the game device 100 accumulates information indicating the acquired elapsed time.

Step S5-2

The derivation unit 150c of the game device 100 determines whether the information indicating the elapsed time has been accumulated for the number of measurement operations. If the information indicating the elapsed time has not been accumulated for the number of measurement operations, the operation proceeds to step S1-2.

Step S6-2

The derivation unit 150c of the game device 100 derives a statistical value such as a mean on the basis of the information indicating the elapsed time accumulated for the number of measurement operations. Further, a value is not limited to a mean, and various statistical values such as a median, a maximum, and a mode may be used. Here, a case in which a statistical value is derived using a mean will be continuously described as an example.

Step S7-2

The output unit 150d of the game device 100 acquires information indicating the statistical value from the derivation unit 150c. The output unit 150d determines whether the statistical value is equal to or greater than a threshold value on the basis of the acquired information indicating the statistical value. If the statistical value is not equal to or greater than the threshold value, the operation ends. For example, a statistical value at the time at which the game started is set as the threshold value, and it is determined whether the statistical value derived at this time is equal to or greater than the threshold value. That is, it is determined whether the reaction speed has deteriorated as the elapsed time becomes longer. Further, comparison of the statistical value with the threshold value is not limited to determining whether the statistical value is equal to or greater than the threshold value, and comparison may be performed on the basis of whether the difference between the statistical value and the threshold value is equal to or greater than a predetermined value.

Step S8-2

The output unit 150d of the game device 100 displays a warning if the statistical value is equal to or greater than the threshold value.

Although a case in which one input device 50 is connected to the game device 100 has been described in the above embodiment, the invention is not limited thereto. For example, a plurality of input devices 50 may be connected to the game device 100.

Although a case in which the left grip part, the right grip part, the direction keys, the operation buttons, and the touch pad are provided as examples of the input device 50 has been described in the above embodiment, the invention is not limited thereto. For example, the input device 50 may include a controller with a motion sensor including an acceleration sensor, a gyro sensor, and the like. In addition, along with or instead of the input device 50, the game device 100 may recognize gesture operations of the user U using a camera provided in the device, and may create instruction information on the basis of the recognized result.

Although a case in which the game device 100 reads a program, data, or the like from a ROM medium loaded in the media drive 155 has been described in the above embodiment, the invention is not limited thereto. For example, the game device 100 may download a game application.

Although a case in which the game device 100 requires the user U to continuously perform an operation of pressing a specific button by outputting sound of an aircraft such as a helicopter flying "chak, chak, chak, . . . " to the output device 10 and a case in which the game device 100 requires the user U to perform an operation of repeatedly pressing a specific button by outputting a speech of a comrade calling for help "help" to the output device 10 in a scene of the game have been described in the above embodiment, the invention is not limited thereto. A sound and an operation required for the user U can be appropriately set.

Although a case in which, if the determination unit 150b of the game device 100 determines to start measuring the degree of fatigue, the derivation unit 150c starts measuring the degree of fatigue of the user U each time in a scene of the game has been described in the above embodiment, the invention is not limited thereto. For example, if the determination unit 150b of the game device 100 determines to start measuring the degree of fatigue, the derivation unit 150c may start measuring the degree of fatigue of the user U in a scene of the game at a predetermined rate or on the basis of a probability.

Although a case in which the game device 100 derives the degree of fatigue on the basis of both a reaction speed and agility in an operation has been described in the above embodiment, the invention is not limited thereto. For example, the game device 100 may derive the degree of fatigue on the basis of either a reaction speed or agility in an operation.

Although a case in which the output unit 150d of the game device 100 displays the information indicating that the user U is encouraged to take a rest has been described in the above embodiment, the invention is not limited thereto. For example, the output unit 150d may display information indicating a reaction speed and information indicating agility in addition to the information indicating that the user U is encouraged to take a rest. In this case, the output unit 150d may acquire the information indicating the reaction speed and information indicating agility from the derivation unit 150c. The output unit 150d may display the information indicating the reaction speed and information indicating agility on the output device 10. Here, the output unit 150d may store information indicating past reaction speeds in the storage unit 165a and display information indicating the time series of reaction speeds including the acquired information indicating the reaction speed and the information indicating the past reaction speeds. In addition, the output unit 150d may store information indicating past agility in the storage unit 165a and display information indicating the time series of agility including the acquired information indicating agility and the information indicating the past agility.

Although a case in which the output unit 150d displays the information acquired from the derivation unit 150c (information indicating the degree of fatigue) on the output device 10 has been described in the above embodiment, the invention is not limited thereto. For example, the information derived by the derivation unit 150c (information indicating the degree of fatigue) may be transmitted to another terminal (not illustrated). In this case, the other terminal receives information transmitted by the game device 100 and outputs the received information. With the configuration described above, in a case in which the user U is a child and the other terminal is a terminal of a parent of the child, the parent can be notified of the degree of fatigue of the child while the game progresses.

In the above-described embodiment, the output unit 150d is optional, and may be omitted.

According to the game system 1 of the present embodiment, the game device 100 includes the reception unit 150a that receives instruction information created when a user performs an operation on the input device triggered by a sound output while a game progresses, a derivation unit 150c that starts measuring the degree of fatigue on the basis of the instruction information received by the reception unit 150a and derives the degree of fatigue of the user on the basis of an operation performed by the user during the started measurement of the degree of fatigue, and the output unit 150d that outputs information indicating the degree of fatigue derived by the derivation unit 150c. By making a characteristic sound for a start of an event, it is possible to make the user be aware of it regardless of a direction of attention of the user. Thus, it is possible to present the user from being unaware of the start of measurement of the degree of fatigue. In addition, because measurement of the degree of fatigue is started on the basis of the instruction information received triggered by the sound, fatigue can be measured in an event in a game, without letting the user notice.

In addition, the game device includes the storage unit 165a that stores one or a plurality of sound IDs and information indicating content of an operation performed by the user in association with each other, and the determination unit 150b that acquires the information indicating the content of the operation stored in association with the sound ID output while a game progresses from the storage unit 165a and determines whether the acquired information indicating the content of the operation matches information indicating content of an operation included in the instruction information received by the reception unit 150a. If the determination unit 150b determines that the information matches, the derivation unit 150c starts measuring the degree of fatigue, and derives the degree of fatigue of the user U on the basis of an operation performed by the user U during the started measurement of the degree of fatigue. With the configuration described above, if the information indicating the content of the operation stored in association with the sound ID corresponding to the sound output while the game progresses matches the information indicating the content of the operation included in the instruction information received by the reception unit 150a after the sound is output, the degree of fatigue of the user U can be derived.

In addition, the derivation unit 150c derives the degree of fatigue on the basis of either or both of the reaction speed and the agility with respect to an operation. As described above, after measurement of the degree of fatigue is started, by deriving the degree of fatigue using either or both of a reaction speed and an agility with respect to an operation as an index, the accuracy in the measurement of fatigue can be improved.

In addition, the derivation unit 150c derives the degree of fatigue on the basis of either of the number of repeated hits made by the user U within a predetermined time period during the measurement of the degree of fatigue and the time required for a predetermined number of repeated hit operations. With the configuration described above, the degree of fatigue of the user U can be derived on the basis of an operation of the user U while the game progresses.

Modified Example of Embodiment

FIG. 1 can be applied to a configuration example of a game system 1a according to a modified example of the embodiment of the present invention. However, differences are that a game device 100a-1 to a game device 100a-n are included in place of the game device 100-1 to the game device 100-n and a game server 200a is included in place of the game server 200.

Hereinafter, any game device among the game device 100a-1 to the game device 100a-n will be described as a game device 100a. In addition, an input device connected to the game device 100a will be described as an input device 50, and a user using the game device 100a and the input device 50 will be described as a user U.

The user U performs an operation on the input device 50 triggered by a sound output in a predetermined scene while a game progresses. The input device 50 detects the operation performed by the user U and creates instruction information including the user ID and information indicating content of the operation on the basis of the detected operation. The input device 50 outputs the created instruction information to the game device 100a. The game device 100a transmits the instruction information to the game server 200a upon receiving the instruction information output by the input device 50.

The game server 200a receives the instruction information transmitted by the game device 100a and reflects the content of the operation in the game on the basis of the information indicating the content of the operation included in the received instruction information. The game server 200a transmits game information including game data in which the content of the operation is reflected to the game device 100a that has transmitted the instruction information. The game device 100a receives the game information transmitted by the game server 200a and outputs an image and sound of the game on the basis of the game data included in the received game information.

In addition, the game device 100a starts measuring the degree of fatigue. The user U continues the game by performing an operation with the input device 50. The input device 50 detects the operation performed by the user U and creates instruction information on the basis of the detected operation. The input device 50 outputs the created instruction information to the game device 100a.

The game device 100a receives the instruction information output by the input device 50. The game device 100a derives the degree of fatigue on the basis of the information indicating the content of the operation included in the received instruction information. The game device 100a outputs information indicating the derived degree of fatigue.

Among the input device 50, the game device 100a, and the game server 200a included in the game system 1a, the game device 100a and the game server 200a that are different from those in the above embodiment will be described below.

FIG. 2 can be applied to a hardware configuration of the game device 100a.

Figure 11:
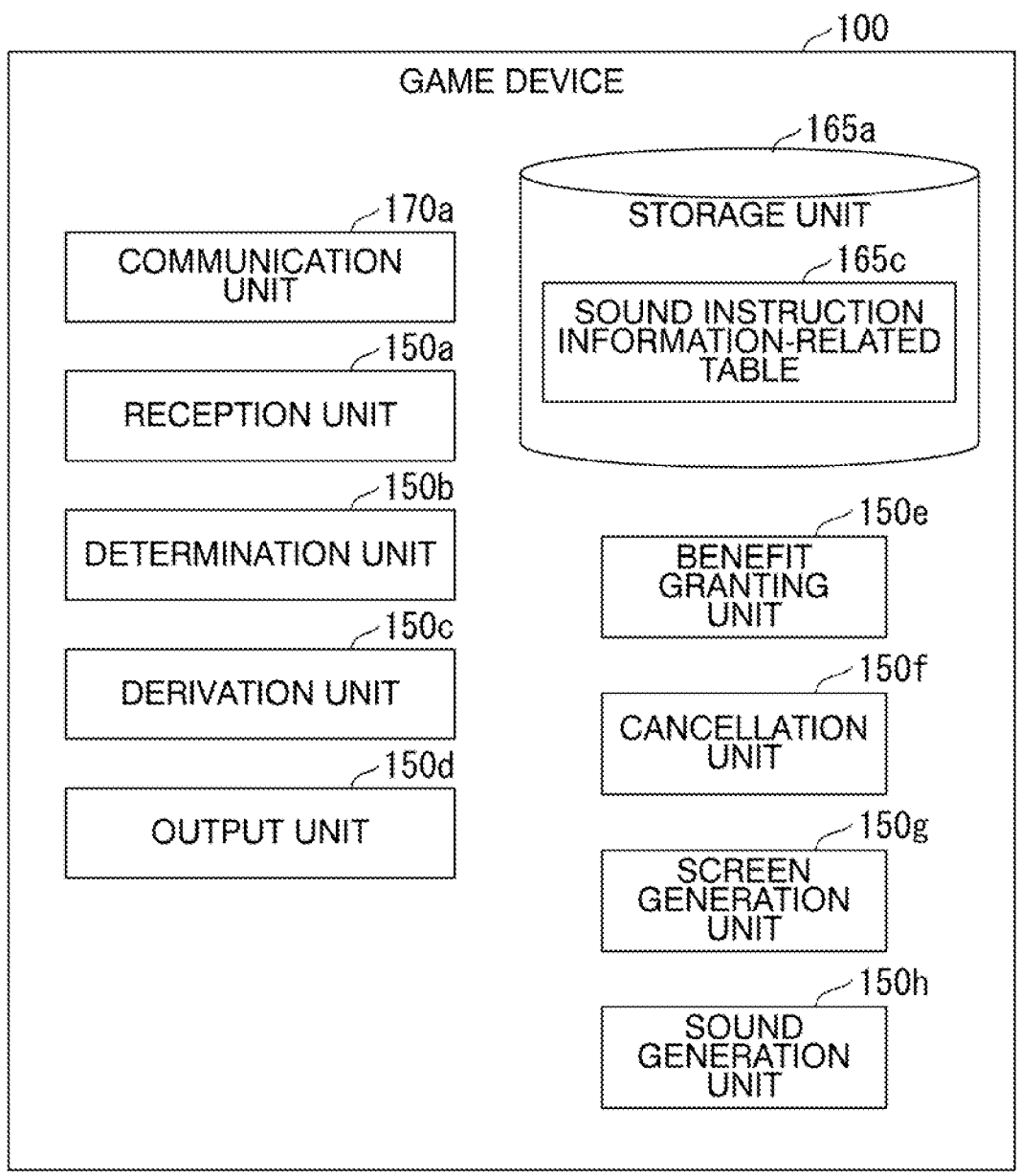
FIG. 11 is a block diagram illustrating an example of a game device according to a modified example of the embodiment.

FIG. 11 is a block diagram illustrating an example of the game device according to the modified example of the embodiment.

The game device 100a includes, for example, a communication unit 170a, a reception unit 150a, a determination unit 150i, a derivation unit 150c, an output unit 150d, a benefit granting unit 150e, a cancellation unit 150f, a screen generation unit 150g, a sound generation unit 150h, and a storage unit 165a.

A sound instruction information-related table 165c is information in a table form in which combinations of one or a plurality of sound IDs with scene IDs, a scene being a situation in which a sound corresponding to a sound ID is output for each of one or a plurality of sound IDs, are associated with information indicating the content of an operation required for the user U. A scene ID is identification information of a scene. Here, an example of a scene is a situation in which an aircraft is approaching a user on a ground, a situation in which a comrade is running, or the like.

The benefit granting unit 150e acquires at least one of a reaction speed, an agility, and a degree of fatigue from the derivation unit 150c, and grants a benefit to the corresponding user on the basis of at least one of the acquired reaction speed, agility, and degree of fatigue. The benefit granting unit 150e may grant a benefit to the user U immediately or when the game resumes. When granting a benefit, the benefit granting unit 150e creates instruction information including the user ID to whom the benefit is granted and information indicating the benefit to be granted and outputs the created instruction information to the communication unit 170a.

In addition, the benefit granting unit 150e may output the information indicating the benefit to be granted to the user U to the output unit 150d. For example, the benefit granting unit 150e may reflect a high or low degree of fatigue in the game. With the configuration described above, the operation to derive the degree of fatigue can be incorporated as a part of the game. In addition, for example, the benefit granting unit 150e may increase or decrease the effect of an item or the number of obtainable items on the basis of at least one of the reaction speed, agility, and degree of fatigue.

The output unit 150d acquires the information indicating the benefit to be granted to the user U output by the benefit granting unit 150e, The output unit 150d displays the acquired information indicating the benefit to be granted to the user U on the output device 10.

The determination unit 150i determines whether a sound has been output in a predetermined scene while the game progresses. Specifically, when a sound is output in a predetermined scene while the game progresses, the determination unit 150i acquires the scene ID of the scene and the sound ID. The determination unit 150i determines whether the combination of the scene ID and the sound ID is stored in the sound instruction information-related table 165c. When it is determined that the combination of the scene ID and the sound ID is stored in the sound instruction information-related table 165c, the determination unit 150i determines that the sound has been output in the predetermined scene. When it is determined that the sound has been output in the predetermined scene, the determination unit 150l acquires information indicating the content of an operation stored in association with the sound ID corresponding to the sound from the sound instruction information-related table 165c of the storage unit 165a. The determination unit 150i determines whether the acquired information indicating the content of the operation matches the information indicating the content of the operation included in the instruction information received by the reception unit 150a. If it is determined that the information matches, the determination unit 150i determines to start measuring the degree of fatigue.

The game server 200a includes an item management unit (not illustrated) in the above-described game server 200. The item management unit manages parameters of items, points, and the like acquired by the user U of the game device 100a. The item management unit acquires the instruction information received by the communication unit 275a and manages parameters of items, points, and the like on the basis of the user ID included in the acquired instruction information and the information indicating a benefit to be granted.

Operation of Game System 1a

FIG. 9 can be applied to an example of an operation of the game system according to the modified example of the embodiment.

Figure 12:
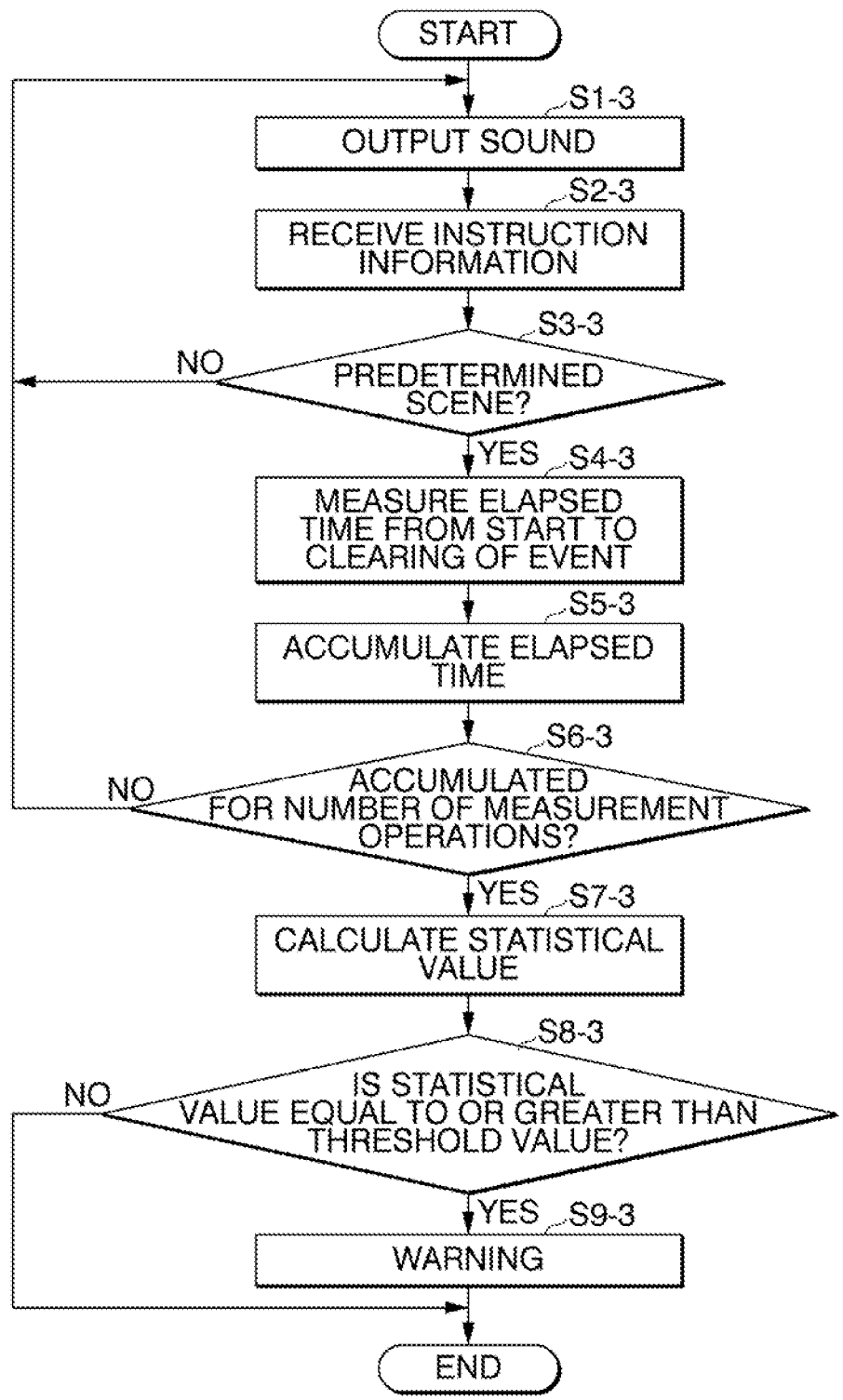
FIG. 12 is a flowchart showing an example of an operation of a game system according to the modified example of the embodiment.

FIG. 12 is a flowchart showing an example of an operation of the game system according to the modified example of the embodiment. In FIG. 12, details of the inspection process of step S2-1 of FIG. 9 are mainly described. Here, as an example, a case in which the derivation unit 150c starts an event by outputting a sound to the output device 10 and acquires an elapsed time from the time at which the event is started to a time at which the event is cleared will be described. The acquired elapsed time is regarded as a reaction speed.

Steps S1-1 and S2-1 of FIG. 10 can be applied to steps S1-3 and S2-3.

Step S3-3

The determination unit 150i of the game device 100a determines whether a sound has been output in a predetermined scene. Specifically, the determination unit 150i acquires the scene ID of the scene and the sound ID. The determination unit 150i determines whether the combination of the scene ID and the sound ID is stored in the sound instruction information-related table 165c. When it is determined that the combination of the scene ID and the sound ID is stored in the sound instruction information-related table 165c, the determination unit 150i determines that the sound has been output in the predetermined scene. If it is determined that the sound has been output in the predetermined scene, the operation proceeds to step S4-3, and if not, the operation proceeds to step S1-3.

Steps S3-2 to S8-2 of FIG. 10 can be applied to steps S4-3 to S9-3.

Although a case in which the operation ends if the statistical value is not equal to or greater than the threshold value in step S8-3 in FIG. 12 has been described, the invention is not limited thereto. For example, the output unit 150d may display the information indicating the benefit to be granted to the user U on the output device 10.

In addition, even when the warning is displayed in step S9-3, the output unit 150d may display the information indicating the benefit to be granted to the user U on output device 10.

According to the game system 1a according to the modified example of the embodiment, the game device 100a includes the storage unit 165a that stores a combination of one or a plurality of sound IDs and a scene ID and information indicating content of an operation performed by a user in association with each other, and the determination unit 150i that acquires a sound ID output while a game progresses and a scene ID of a scene in which a sound has been output and determines whether a combination of the acquired sound ID and scene ID is stored in the storage unit 165a, in addition to the functions of the game device 100. If it is determined that the combination of the sound ID and the scene ID is stored in the storage unit 165a, the determination unit 150i acquires the information indicating the content of the operation stored in association with the combination of the sound ID and the scene ID from the storage unit 165a and determines whether the acquired information indicating the content of the operation matches information indicating content of an operation included in the instruction information received by the reception unit 150a. If the determination unit 150i determines that the information matches, the derivation unit 150c starts measuring the degree of fatigue, and derives the degree of fatigue of the user on the basis of an operation performed by the user during the started measurement of the degree of fatigue.

With the configuration described above, when a sound is output in a predetermined scene while a game progresses, the game device 100a acquires the sound ID corresponding to the sound and the scene ID of the scene in which the sound has been output, and determines whether the combination of the acquired sound ID and scene ID is stored in the storage unit 165a. If it is determined that the combination is stored and the instruction information stored in association with the sound ID matches instruction information received by the reception unit 150a after the sound is output, the game device 100a derives the degree of fatigue of the user U. Because it is necessary for the user U to determine whether a sound has been output in a predetermined scene and perform an operation, a degree of fatigue of the user U can be reflected more.

In addition, the benefit granting unit 150e that grants a benefit to the user on the basis of the degree of fatigue derived by the derivation unit 150c is further included. With the configuration described above, because a benefit can be granted to the user U on the basis of the degree of fatigue, measurement of the degree of fatigue while the game progresses can be encouraged. In addition, it is possible to encourage the user U to perform measurement stably by providing an advantage according to the result of the measurement on the basis of the degree of fatigue in the game.

Although the embodiment and the modified example of the present invention have been described in detail above referring to the drawings, a specific configuration is not limited to the embodiment and the modified example and includes an amendment to a design that falls within the scope that does not depart from the gist of the present invention. The embodiment and modified example thereof can be implemented in other various modes, and can be subject to various omission, replacement, modification, and combination within the scope not departing from the gist of the invention. The embodiment and modified example thereof are included in the scope and gist of the invention, and at the same time, included in the inventions described in the claims and equivalents thereof.

For example, a computer program for realizing the functions of each device described above may be recorded in a computer-readable recording medium, and the computer program recorded in the recording medium may be read by a computer system to be executed. Further, the "computer system" mentioned here may include an OS and hardware such as a peripheral apparatus.

In addition, the "computer-readable recording medium" refers to a writable non-volatile memory such as a flexible disk, a magneto-optical disk, a ROM, or a flash memory, a portable medium such as a digital versatile disc (DVD), or a storage device such as a hard disk built into the computer system.

Moreover, the "computer-readable recording medium" may include a medium that retains a program for a certain time period, like a volatile memory (e.g., a dynamic random access memory (DRAM)) within the computer system for functioning as a server or a client in a case in which a computer program is transmitted over a network such as the Internet or over a communication line such as a telephone line.

In addition, the program may be transmitted to another computer system from the computer system saving the program in a storage device, or the like via a transmission medium or by transmission waves in a transmission medium. Here, the "transmission medium" for transmitting the program refers to a medium with the function of transmitting information such as a network (communication network) like the Internet or a communication line such as a telephone line.

In addition, the program may realize some of the above-described functions. Furthermore, the program may be a so-called differential file (differential program) that can realize the above-described functions in combination of a program already recorded in the computer system.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES 1, 1a Game system
10 Output device
50-1, . . . , 50a-n, 50-n, . . . , 50 Input device
100-1, . . . , 100-n, 100a-1, . . . , 100a-n, 100, 100a Game device
   110 System controller
   120 Clock
   130 Device controller
   140 Subsystem
   150 Main system
   150a Reception unit
   150b, 150i Determination unit
   150c Derivation unit
   150d Output unit
   150e Benefit granting unit
   150g Screen generation unit
   150h Sound generation unit
   155 Media drive
   160 USB module
   165 Flash memory
   165a Storage unit
   165b, 165c Sound instruction information-related table
   170 Wireless communication module
   170a Communication unit
   175 Wired communication module
200 Game server
   275a Communication unit
   250a Player management unit
   250b Game control unit
   250h Storage unit
   250i Player DB

What is claimed is:

1. A game device comprising:
a processor that is configured to receive instruction information created when a user performs an operation on an input device triggered by a sound output while a game progresses, and to start measuring a degree of fatigue on a basis of the instruction information received and derives a degree of fatigue of the user on a basis of an operation performed by the user during the started measurement of a degree of fatigue; and
a memory that is configured to store one or a plurality of pieces of identification information of sounds and information indicating content of an operation performed by the user in association with each other,
wherein the processor acquires, from the memory, the information indicating a content of the operation stored in association with the identification information of a sound output while the game progresses, determines whether the acquired information indicating the content of the operation matches information indicating content of an operation included in the instruction information received,
if the information matches, starts measuring a degree of fatigue and derives a degree of fatigue of the user on a basis of the operation stored in association with the sound identification information performed by the user during the started measurement of a degree of fatigue, output a warning based on the degree of fatigue of the user derived.

2. The game device according to claim 1,
wherein the memory stored a combination of one or a plurality of pieces of identification information of sounds and identification information of a scene and information indicating content of an operation performed by a user in association with each other,
wherein the processor acquires the identification information of a sound output while the game progresses and the identification information of a scene in which the sound has been output and determines whether a combination of the acquired identification information of the sound and the identification information of the scene is stored in the memory,
if determined the combination of the identification information of the sound and the identification information of the scene is stored in the memory, acquires, from the memory, information indicating content of an operation stored in association with the combination of the identification information of the sound and the identification information of the scene, and determines whether the acquired information indicating the content of the operation matches the information indicating the content of the operation included in the instruction information received,
if the information matches, starts measuring a degree of fatigue and derive a degree of fatigue of the user on the basis of the operation performed by the user during the started measurement of a degree of fatigue.

3. The game device according to claim 1,
wherein the processor derives the degree of fatigue on the basis of either or both of a reaction speed and an agility with respect to the operation.

4. The game device according to claim 1,
wherein the processor derives the degree of fatigue on the basis of either of a number of repeated hits made by the user within a predetermined time period during the measurement of a degree of fatigue and a time required for a predetermined number of repeated hit operations.

5. The game device according to claim 1,
wherein the processor grants a benefit to the user on the basis of the degree of fatigue derived.

6. The game device according to claim 1, wherein the processor outputs the warning based only on the degree of fatigue of the user derived, regardless of the progress of the game.

7. The game device according to claim 1, wherein the processor outputs the warning without changing the progress of the game.

8. A method comprising:
receiving instruction information created when a user performs an operation on an input device triggered by a sound output while a game progresses;
acquiring the information indicating a content of the operation stored in association with the identification information of a sound output while the game progresses from a memory that stores one or a plurality of pieces of identification information of sounds and information indicating content of an operation performed by the user in association with each other:

determining whether the acquired information indicating the content of the operation matches information indicating content of an operation included in the instruction information received;

starting measuring a degree of fatigue if the information matches;

deriving a degree of fatigue of the user on a basis of the operation stored in association with the sound identification information performed by the user during the started measurement of a degree of fatigue; and outputting a warning based on the degree of fatigue of the user derived.

9. The method of claim 8, further comprising:

acquiring the identification information of a sound output while the game progresses and the identification information of a scene in which the sound has been output and determining whether a combination of the acquired identification information of the sound and the identification information of the scene is stored in the memory that stores a combination of one or a plurality of pieces of identification information of sounds and identification information of a scene and information indicating content of an operation performed by a user in association with each other, if determined the combination of the identification information of the sound and the identification information of the scene is stored in the memory, acquiring information indicating content of an operation stored in association with the combination of the identification information of the sound and the identification information of the scene, and determining whether the acquired information indicating the content of the operation matches the information indicating the content of the operation included in the instruction information received, and if the information matches, starting measuring a degree of fatigue and derive a degree of fatigue of the user on the basis of the operation performed by the user during the started measurement of a degree of fatigue.

10. The method of claim 8, wherein the deriving includes deriving the degree of fatigue on the basis of either or both of a reaction speed and an agility with respect to the operation.

11. The method of claim 8, wherein the deriving includes deriving the degree of fatigue on a basis of either of a number of repeated hits made by the user within a predetermined time period during the measurement of a degree of fatigue and a time required for a predetermined number of repeated hit operations.

12. The method of claim 8, further comprising:

granting a benefit to the user on the basis of the degree of fatigue derived.

13. A non-transitory computer readable medium storing a program causing a computer to execute:

receiving instruction information created when a user performs an operation on an input device triggered by a sound output while a game progresses;

acquiring the information indicating a content of the operation stored in association with the identification information of a sound output while the game progresses from a memory that stores one or a plurality of pieces of identification information of sounds and information indicating content of an operation performed by the user in association with each other;

determining whether the acquired information indicating the content of the operation matches information indicating content of an operation included in the instruction information received; and starting measuring a degree of fatigue if the information matches:

deriving degree of fatigue of the user on a basis of the operation stored in association with the sound identification information performed by the user during the started measurement of a degree of fatigue; and outputting a warning based on the degree of fatigue of the user derived.

14. The non-transitory computer readable medium of claim 13, further storing a program causing the computer to execute:

acquiring the identification information of a sound output while the game progresses and the identification information of a scene in which the sound has been output and determining whether a combination of the acquired identification information of the sound and the identification information of the scene is stored in the memory that stores a combination of one or a plurality of pieces of identification information of sounds and identification information of a scene and information indicating content of an operation performed by a user in association with each other, if determined the combination of the identification information of the sound and the identification information of the scene is stored in the memory, acquiring information indicating content of an operation stored in association with the combination of the identification information of the sound and the identification information of the scene, and determining whether the acquired information indicating the content of the operation matches the information indicating the content of the operation included in the instruction information received, and if the information matches, starting measuring a degree of fatigue and derive a degree of fatigue of the user on the basis of the operation performed by the user during the started measurement of a degree of fatigue.

15. The non-transitory computer readable medium of claim 13, wherein the deriving includes deriving the degree of fatigue on the basis of either or both of a reaction speed and an agility with respect to the operation.

16. The non-transitory computer readable medium of claim 13, wherein the deriving includes deriving the degree of fatigue on a basis of either of a number of repeated hits made by the user within a predetermined time period during the measurement of a degree of fatigue and a time required for a predetermined number of repeated hit operations.

17. The non-transitory computer readable medium of claim 13, further comprising:

granting a benefit to the user on the basis of the degree of fatigue derived.

* * * * *